United States Patent [19]

Yoo

[11] 4,010,216
[45] Mar. 1, 1977

[54] CODIMERIZATION PROCESS USING A SUPPORTED NICKEL CARBONYL CATALYST

[75] Inventor: Jin Sun Yoo, South Holland, Ill.

[73] Assignee: Atlantic Richfield Company, Philadelphia, Pa.

[22] Filed: Apr. 14, 1975

[21] Appl. No.: 568,211

Related U.S. Application Data

[62] Division of Ser. No. 314,147, Dec. 11, 1972, Pat. No. 3,907,923, which is a division of Ser. No. 49.968, June 25, 1970, Pat. No. 3,725,306.

[52] U.S. Cl. .................. 260/680 R; 260/683.15 D
[51] Int. Cl.² ...................... C07C 11/12; C07C 3/10
[58] Field of Search .......................... 252/430, 443; 260/680 R, 683.15

[56] References Cited

UNITED STATES PATENTS

| | | | |
|---|---|---|---|
| 2,448,375 | 8/1948 | Larson | 252/443 X |
| 2,969,408 | 1/1961 | Nowlin et al. | 260/683.15 |
| 3,134,824 | 5/1964 | Walker et al. | 260/683.15 |
| 3,277,099 | 10/1966 | Seibt et al. | 260/666 |
| 3,306,948 | 2/1967 | Kealy | 260/680 |
| 3,355,510 | 11/1967 | Cannell et al. | 260/683.15 |
| 3,536,778 | 10/1970 | Bergem | 260/683.15 |
| 3,592,869 | 7/1971 | Cannell | 260/683.15 |
| 3,631,121 | 12/1971 | Hutson | 260/683.15 D |

Primary Examiner—Oscar R. Vertiz
Assistant Examiner—Brian E. Hearn
Attorney, Agent, or Firm—Thomas J. Clough

[57] ABSTRACT

A novel codimerization process using a heterogeneous, nickel-containing catalysts comprising
A. A nickel carbonyl complex, and
B. An acidic, solid, silica-based material are active in co-dimerization, of various olefins. In specific aspects, bis(triphenylphosphine) nickel dicarbonyl supported on an acidic, calcined, silica-alumina support containing a separate alumina phase, is active in, the codimerization of a conjugated diene and an alpha-olefin.

18 Claims, No Drawings

CODIMERIZATION PROCESS USING A SUPPORTED NICKEL CARBONYL CATALYST

This is a division of application Ser. No. 314,147, filed Dec. 11, 1972, now U.S. Pat. No. 3,907,923, issued Sept. 23, 1975, which application is a division of application Ser. No. 49,968, filed June 25, 1970, now U.S. Pat. No. 3,725,306.

This invention relates to novel, heterogeneous, nickel carbonyl complex containing catalysts useful in the homodimerization, codimerization, oligomerization and polymerization of various olefinic compounds. In more particular aspects, this invention concerns a supported, heterogeneous catalyst comprising a nickel carbonyl complex and an acidic, solid, silica-based support material.

Unsupported, homogeneous catalysts containing certain nickel complexes, with or without certain Lewis acids as a component, have been disclosed in the prior art as useful catalytic species for enhancing the cyclooligomerization of 1,3-butadiene. Also, unsupported, homogeneous catalysts containing certain nickel complexes and Lewis acids have been studied regarding the oligomerization of olefins. The use of such catalysts in liquid form is noted in U.S. Pat. Nos. 3,243,468; 3,414,629 and 3,468,921 and in the literature in a paper, G. Hata and A. Miyake, *Chem. Ind. London*, p. 921 (1967).

The heterogeneous catalysts of this invention, however, overcome numerous disadvantages attendant the use of such prior art catalytic species. The use of the solid catalysts of this invention, in, for example, a fixed bed or in a slurry form, eliminates the necessity for the separation of the soluble catalytic species from the reaction products and thus eliminates catalyst losses normally occurring during such separations. Also, since the nickel carbonyl complex of the catalyst herein is firmly fixed upon the acidic, solid, silica-based support material, probably either through a coordination bond or through an electrostatic ionic bond formed through an ion exchange mechanism, the catalyst is remarkably stable and active for long periods of time. Furthermore, the level of catalytic activity exhibited by the solid catalysts of this invention is normally substantially higher than in the corresponding homogeneous catalysts; in fact, most of the nickel carbonyl complexes useful herein exhibit very slight or no catalytic activity whatsoever in the absence of the support material. Therefore, the acidic, solid, silica-based material useful herein functions not only as a support but also as a cocatalyst. Also, the heterogeneous catalysts of this invention are useful for selective oligomerization, particularly dimerization processes.

The nickel complexes useful in the catalysts of this invention include as an essential ingredient nickel carbonyl complexes of the formula:

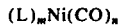

wherein L is a tertiary, essentially hydrocarbyl-substituted monodentate ligand of a Group V-A element and $m$ is an integer value from 0 to 3, preferably at least one, and $n$ is an integer value of 1 to 4, the sum of $m$ and $n$ being 4. In essence, the nickel atom in the above represented compounds has at least one and up to and including four carbonyl groups associated through a bond therewith. Thus, $n$ plus the number of Group V-A element atoms associated with the nickel is four. The preparation of complexes containing the nickel carbonyl compounds represented by the above formula is well known in the art. Advantageously, however, the nickel complex might be prepared by the reaction of a nickel source such as an inorganic salt with carbon monoxide and optionally and preferably a Group V-A element monodentate ligand in a suitable solvent, such as hydrocarbon solvents. Preferably, the nickel compounds of the above formula are than separated from the mixture and used themselves as the nickel complex. The reaction mixture, however, might be used; the use thereof provides for the in situ preparation of the nickel carbonyl compounds and simultaneous or subsequent impregnation upon the acidic, solid, silica-based support and cocatalytic material of this invention.

The tertiary, hydrocarbyl-substituted monodentate ligand of a Group V-A element useful in this invention include those represented by the formula:

wherein Y is a Group V-A element, i.e., nitrogen, phosphorus, arsenic, antimony or bismuth, $p$ is 2 or 3, and R is a mono-or divalent essentially hydrocarbon moiety. Thus, these Group V-A ligands are amines, phosphines, arsines, stibines and bismuthines. The mono and divalent hydrocarbon groups include alkyl, aryl, alkaryl, aralkyl, cycloalkyl and alkylene groups, all of which groups can have up to about 20 or more carbon atoms. When the R groups are all monovalent hydrocarbyl groups, $p$ is 3, and when one R group is a divalent hydrocarbylene group, $p$ is 2. Among the useful R groups are for example methyl, ethyl, isobutyl, butyl, hexyl, decyl, octadecyl, phenyl, biphenyl, β-naphthyl, β-naphthyl, phenanthryl, tolyl, xylyl, mesityl, duryl, cumenyl, benzyl, phenethyl, cyclooctyl, cyclopentyl, cyclooctl, 3-methylcyclohexyl, butylene and hexylene. The preferred Group V-A element ligands for the nickel complexes of this invention are the tertiary mono phosphines. Exemplary of these are trimethylphosphine, triethylphosphine, tripropylphosphine, trioctylphosphine, tridecylphosphine, dimethylethylphosphine, triphenylphosphine, tri(o-tolyl)phosphine, tricyclobutylphosphine, tricyclopentylphosphine, tribenzylphosphine, diphenylbenzylphosphine and methyl butylene phosphine. The corresponding amines, arsines, stibines and bismuthines are also useful. Amine complexes such as bis(pyridyl) nickel dicarbonyl are also useful. The most advantageous nickel complexes have been found to be those wherein both $m$ and $n$ are two such as bis(trihydrocarbylphosphine) nickel dicarbonyls, for example, bis(triphenylphosphine) nickel dicarbonyl. Also, nickel tetracarbonyl is useful.

The solid support of the catalyst of the present invention is an acidic, silica-based material, e.g., having a D + L activity of at least about 20, preferably at least about 30 when determined according to the method of Birkhimer et al., "A Bench Scale Test method for Evaluating Cracking Catalysts," Proceedings of the American Petroleum Institute, Division of Refining, Vol. 27 (III), page 90 (1947), and hereinafter referred to as Cat A. The silica-based support preferably has a substantial surface area as determined by the BET nitrogen absorption procedure (JACS, Vol. 60, pp. 309 et seq.) (1938). The surface area of the support can be at least about 50 square meters per gram, and such surface areas are often up to about 500 or more m²/gm., preferably about 150 to 400 m²/gm. It is preferred that the catalyst support be relatively dry to avoid undue reaction with and loss of catalytic promoting materials. Thus, it is advantageous that the support be calcined, e.g., at temperatures of about 600° to 1500° F or more, to reduce the water content, but such calcination should not be so severe that the support is no longer sufficiently catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites comtemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings in the 6 to 15 Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogen with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500° F. to convert the silica-alumina hydrogel to xerogel form. The dried material can then be calcined, e.g., at a temperature of about 700° to 1500° F., preferably about 800° to 1400° F., to provide the active catalyst support. During calcination, the separate hydrous alumina phase of the mixture is converted to a gamma form or other catalytically active alumina.

In providing the preferred catalyst support precursor for drying, the components can be combined in any suitable manner or order desired, and advantageously each of the components is in the mixture in finely divided form, preferably the particles are principally less that about 300 mesh in size. The finely divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 to ½ inch or more in diameter and about 1/32 to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogen which contains about 55 to 90, preferably 65 to 75, weight percent silica and about 10 to 45, preferably about 25 to 35, weight percent alumina, on a dry basis. The silica-alumina can be naturally occurring or can be synthetically prepared by any desired method and several procedures are known in the art. For instance, an amorphous silica-alumina hydrogel can be prepared by coprecipitation or sequential precipitation by either component being the initial material with at least the principal part of the silica or alumina being made in the presence of the other. Generally, the alumina is precipitated in the presence of a silica gel. It is preferred that the silica-alumina hydrogel be made by forming a silica hydrogen by precipitation from an alkali metal silicate solution and an acid such as sulfuric acid. Then alum solution may be added to the silica hydrogen slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, one may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water washed to acceptable concentrations of, for instance, sodium, and redried in the preferred procedure. The drying, especially the initial drying, is advantageously effected by spray drying to give microspheres.

The crystalline aluminosilicate which can be present in catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-A and rare earth metals such as cerium, etc. The metals may be present alone with the ammonium or hydrogen cations.

The catalysts of this invention contain a minor, catalytically effective amount of nickel complex and a major amount of the support, e.g., from about 2 to 2000 parts by weight of acidic, solid, silica-based support material: 1 part by weight of nickel carbonyl complex. The preferred weight ratio of acidic, solid, silica-based material to nickel carbonyl complex is from about 5 to 200:1.

The catalyst compositions of this invention may be prepared by mixing the acidic, solid, silica-based material with a solution or suspension of the isolated or in situ prepared nickel carbonyl complex in an inert organic solvent at about room temperature or above, i.e., 60° to 300° F. or higher. Normally, mixture at the lower temperatures within the range is sufficient to form an active catalyst species. The mixture of catalyst components is generally stirred vigorously under a nitrogen atmosphere for periods ranging from 5 minutes to a few hours during the preparation of the active heterogeneous catalysts of this invention. Preferably, however, only the nickel carbonyl compound itself is thus added to the support material.

The supported catalysts of this invention are active in the homodimerization, codimerization, oligomerization, and polymerization of olefinic compounds. For example, the catalysts of this invention are useful in the oligomerization of ethylene and propylene to form a major portion of the corresponding dimers and a minor portion of higher oligomerization products. Normally, the oligomerization reactions are accomplished at mild conditions, e.g., in the temperature range of from about −30° to 300° F. The preferred temperature range is from about 100° to 200° F. under pressures of up to about 2000 psig or greater. Pressures of less than about 500 psig are normally used. The reaction times may range from as little as a few minutes to about 20 hours. Substantial reaction is normally accomplished at from about 1 to 5 hours.

Moreover, the supported catalysts of this invention have been found to be useful in the codimerization of 1,3-conjugated diolefins having, for instance, 4 to about 12 carbon atoms, and alpha-olefins having from 2 to 10 carbon atoms to form a major portion of codimerization product. More specifically, 1,3-butadiene and its alkyl, aryl and halogen-substituted derivatives such as isoprene, piperylene, 2-phenyl-1,3-butadiene or chloroprene are codimerized with alpha-olefins of the formula $RCH=CH_2$ wherein R is hydrogen or a hydrocarbyl group of 1 to about 8 carbon atoms, preferably lower alkyl, to form a major portion of various hexadiene products. Generally, reaction conditions previously described as useful regarding the oligomerization reactions are also useful in the codimerization of 1,3-conjugated dienes and alpha-olefins.

The polymerization of the 1,3-conjugated dienes, say of 4 to about 12 carbon atoms, may also be accomplished using the catalysts of this invention under similar reaction conditions. The higher molecular weight portions of the products from the previously described codimerization of conjugated dienes and an alpha-olefin are thus probably predominantly homopolymers of the conjugated diene. These homopolymers are generally viscous, liquid polymers of the previously described conjugated dienes, e.g., those of 4 to about 12 carbon atoms, such as 1,3-butadiene.

The amount of catalyst composition useful in the reactions pof this invention is that sufficient to effect the desired reaction of the olefin feed or feeds. Thus, the essential requirement is that a catalytically effective amount of the compositions of this invention be present in the reaction mixture. Normally, this amount ranges from about 0.01 to 25 percent by weight based on the weight of the reactant or reactants or a weight hourly space velocity of about 0.5 to 15, preferably about 2 to 6.

The preparation of an acidic, silica-alumina support of this invention is illustrated by Examples I to III. This support contains a separate alumina phase.

EXAMPLE I

An alumina hydrogel is prepared as follows:

In a tank containing 5700 gallons of water at 85° F. are dissolved 300 lbs. of soda ash. When the soda ash has been dissolved, 180 gallons of a 39% concentration aqueous sodium aluminate solution are pumped into the tank in about a 15-minute period. The contents of the tank are at about 84° F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons and 39% concentration aqueous sodium aluminate solution which, while being added, is also diluted continuously with water at a rate of 35 gallons per minute over a 7½ minute addition period. The contents of the tank are heated to about 100° F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90° F., and 865 gallons of sodium silicate solutions (28.8 weight percent $SiO_2$, 40–41.5 Baume at 68° F. and $Na_2O:SiO_2$ ratio of 1:3.2) is added. The batch is stirred for five minutes. The concentration of the sodium silicate, as $SiO_2$, in the batch is 6.3 weight percent.

With the batch at 90° F., 302 gallons of 34.5 weight percent sulfuric acid solution at 182° F. are added over a period of 45 minutes. The gel forms about 35 minutes after acid solution is begun. Then the pH is adjusted to 8.0–8.5. The batch is agitated for ten minutes.

Then 715 gallons of alum (7.8 weight percent, as $Al_2O_3$) is added to the gel over a period of about 36 minutes. The batch is agitated for an additional 5 minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for 1 hour. The finished batch has a pH of 5.5 to 5.6 and a temperature of about 110° F. The aqueous gel mixture is then pumped to a dewatering filter and the filter cake from said dewatering filter and a portion of aqueous gel are blended to give a gel slurry of about 14 weight percent solids. A portion of this hydrogel mixture was slurried, as a thick, flowable paste, with a "Lightnin" stirrer fitted with a cage-beater and a propellor, for about 10 minutes to give a thorough dispersion. The product was stirred 1 minute at 14,500 rpm, in a Waring Blender and dried in a laboratory spray-drier. The spray-dried material was washed with water to acceptable impurity levels and dried at 230° F. The washed and dried material analyzed 0.08% $SO_4$ and less than 25 ppm $Na_2O$. The dried material as such was used as the catalyst support, as were extruded forms thereof and tablets (pellets) having diameters of about ⅛ inch and lengths of about ⅛ to ½ inch. Before use, the catalyst support was calcined in a muffle furnace by raising the temperature by 300° F. per hour until 1350° F. was reached. This temperature was then held for 3 hours. The calcined particles had a surface area of about 320 to 340 square meters per gram.

Examples IV to XX illustrate the preparation of the catalyst compositions of this invention on the silica-based support and the utilization thereof in various reactive environments.

EXAMPLE IV

Extrudate pellets (10.0 g) of Example III were added to a homogeneous solution of 0.98 millimole of bis(triphenylphosphine) nickel dicarbonyl in 32 ml toluene. Brown pellets resulted after 1½ hours. The liquid phase was removed from the brown pellets, and the pellets were washed with toluene a few times. The resulting supported pellets were transferred to a 300 cc stainless steel autoclave equipped with an air driven stirrer. Five runs described in Examples V to IX were made in series with this catalyst over a 36½ hour period.

EXAMPLE V

In the first run, propylene (67.6 g) was fed to the catalyst in the reactor of Example IV, and was allowed to react with vigorous agitation at 140°–160° F. over a 70 minute period. During this period, the pressure of the system dropped from 240 to 100 psig. A clear reaction mixture was removed from the reactor. All products obtained in the work were analyzed by means of GL-chromatography and hydrogenation techniques. Products in this first run were found to be composed of about 15% 2,3-dimethylbutenes, about 53% 2-methylpentenes, about 16% n-hexenes and about 15% of high boiling products (mostly $C_9$-olefins). The overall conversion of the propylene feed was 87%.

EXAMPLE VI

The second run was started with the 2-hour aged catalyst. Propylene (62.4 g.) was allowed to react for 85 minutes under similar reaction conditions. The product distribution obtained in the second run was essentially the same as that in the previous run and the overall conversion was about 71%.

EXAMPLE VII

In the third run, a mixed feed of propylene and butene-1 was introduced slowly and continuously to the catalyst, which was aged under a mixed atmosphere of air and unreacted propylene for 4½ hours. The mixed feed (1.40 ml) required 90 minutes for addition to the reactor, after which the reaction was discontinued. Analysis of the product showed that the propylene was selectively oligomerized in a conversion of about 90% to about 11% 2,3-dimethylbutnes, about 60% 2-methylpentenes, about 21% n-hexenes and about 5% nonenes, and that butene-1was essentially unconverted. In other words, little codimerization between propylene and butene-1 had taken place with this catalyst. Thus, propylene can be selectively dimerized from the mixture of propylene and butene with the catalyst of this invention. The composition of the mixed feed (propylene and butene-1) used is as follows:

Component: $C_2$, $C_2 = C_3$, $iC_4$, $nC_4$, $C_4 = 1$, $C_4 = 2T$.
Weight %: 0.01, 0.15, 31.18, 0.33, 0.17, 68.14, 0.01.

EXAMPLE VIII

The fourth run was made with the 20-hour aged catalyst. Isobutylene (81 g) was allowed to react under 75–116 psig and 140°–152° F. for a 75 minute period. Only slight pressure drop was observed. It appears that this catalyst is not highly active toward dimerization of isobutylene under the reaction conditions employed since only about 5.0 grams of higher boiling product was formed; however, employment of more drastic reaction conditions would be expected to improve this dimerization.

EXAMPLE IX

In the fifth run, ethylene was allowed to react with the 26½ hour aged catalyst under about 600psig and at 140°–150° F. for a 10 hour period. Ethylene was converted in 61% yield to about 10% isobutene, 66% n-butenes, 6% 2-methylpentenes, 8% 3-methylpentenes, 9% n-hexenes and 4% 3-methylheptenes.

EXAMPLE X

A catalyst was prepared from 0.98 millimole of bis(-triphenylphosphine) nickel dicarbonyl and 10.0 g pellets of Example III in 25 ml toluene. The brown pellets isolated from the liquid phast were transferred to a 300 cc stainless steel bomb. Reactions were allowed to proceed with periodic agitation. Four runs were made with this catalyst over a 313½ hour period. Both the first and second runs were made with propylene under similar conditions. The product distributions obtained in these runs are essentially the same. Details of these results are listed in table IA-B. The third run was made with the 261 hour aged catalyst. Ethylene was reacted in 73% yield to about 61% n-butenes, 8% 2-methylpentenes, 9% 3-methylpentenes, 9% n-hexenes, and 10% 3-methylheptenes. The pressure of the reaction system was maintained at 400–800 psig without applying heat to the system. The reaction proceeded for a 5½ hour period. The fourth run was started with the 312 hour aged catalyst. Isobutylene (84.0 g) was allowed to react with the catalyst under 45–110 psig and 120° F. for about 4 hours, but only little reaction occurred during this run.

EXAMPLE XI

Extrudate pellets of Example II (5.0 g) were added to a homogeneous toluene solution of bis(triphenylphosphine) nickel dicarbonyl (0.99 millimole in 55 ml toluene). After these pellets were kept in the solution for about 20 minutes, propylene (140 ml) was added to the mixture of pellets and liquid. The system was allowed to react under 200–250 psig for 1⅓ hours. The temperature of the system was maintained at 120°–145° F. by the heat liberated in the reaction. A colorless reaction mixture was removed from the autoclave reactor, leaving behind the pellets containing supported bis(triphenylphosphine) nickel dicarbonyl. Propylene was converted in 54% yield to about 14% 2,3-dimethylbutenes, 52% 2-methylpentenes, 17% n-hexenes and 18% $C_8$–$C_9$-olefin products.

EXAMPLE XII

In the second run using the catalyst of Example XI propylene (72.8 g) was again fed to the catalyst pellets, which were left and aged in the autoclave for 3 hours. The reaction proceeded with vigorous agitation at 160–400 psig and 120°–170° F. for 1⅔ hours. During this period, 26.0 g of product was obtained; the product was not analyzed.

EXAMPLE XIII

A homogeneous solution of 0.97 millimoles of bis(triphenylphosphine) nickel dicarbonyl in 55 ml toluene was prepared under a nitrogen atmosphere in an autoclave. Propylene (145 ml) was introduced to this solution. Note that no support pellets were added. The resulting homogeneous liquid system was allowed to react with vigorous stirring under 115–130 psig and 150°–152° F. over a 1½ hour period. However, bis(triphenylphosphine) nickel dicarbonyl alone did not catalyze the oligomerization of propylene. In short, no reaction occurred in this system. Judging from the results obtained from this and the previous examples, it becomes obvious that the support material of Example III is an essential catalyst component as well as an effective supporting base.

TABLE IA

| Example No. | Run No. | Catalyst Component $(\phi_3P)_2Ni(CO)_2$ m mole | Solvent ml toluene | Support g. | Aged Hour | Reaction Conditions Pressure psig | Temperature ° F. | Reaction Period |
|---|---|---|---|---|---|---|---|---|
| V | | <0.98 | — | 10.0 | — | 100–240 | 140–160 | 70 min. |
| VI | | " | — | " | 2 | 150–220 | 140–168 | 85 min. |
| VII | | " | — | " | 4½ | 100–210 | 130–160 | 90 min. |
| VIII | | " | — | " | 20 | 75–116 | 140–152 | 75 min. |
| IX | | " | — | " | 26½ | 600 | 140–150 | 10 hr. |
| | 1st | <0.98 | — | 10.0 | — | 180–300 | 160–150 | 4¾ hr. |
| | 2nd | " | — | " | 242 | 160–300 | 120–160 | 2 hr. |
| X | 3rd | | — | | 261 | 40–800 | Not Recorded | 5½ hr. |
| | 4th | | — | " | 312 | 45–110 | 120 | 4 hr. |
| XI | | 0.99 | Toluene 55 ml | 5.0 | — | 200–250 | 120–145 | 1⅓ hr. |
| XII | | " | — | " | 3 | 160–400 | 120–170 | 1⅔ hr. |
| XIII* | | 0.97 | Toluene 55 ml | — | — | 115–310 | 150–152 | 1½ hr. |

*Homogeneous System

TABLE IB

| Example No. | Run No. | Feed g | Hydrogenation of Product iC₄ | nC₄ | C₅s | 2.3DMC₄ | 2MC₅ | 3MC₅ | nC₆ | Unidentified | 3MC₇ | nC₈ | C₉ | Total Product wt. g. | Conversion % |
|---|---|---|---|---|---|---|---|---|---|---|---|---|---|---|---|
| | | | | | | Wt.% | | | | | | | | | |
| V | | C₃⁻67.6 | — | — | — | 14.90 | 52.89 | — | 15.55 | 4.44 | — | — | 12.21 | 59.9 | 88.6 |
| VI | | C₃⁻62.4 | — | — | — | 14.31 | 54.25 | — | 16.15 | 2.84 | — | — | 12.45 | 44.0 | 70.5 |
| VII | | C₃⁻C₄⁻ 82.6 | — | — | — | 10.71 | 59.76 | — | 20.56 | 4.11 | — | — | 4.86 | 24.1 | based on C₃⁻ 89.7 C₄⁻ ~C.0 |
| VIII | | iC₄⁻81.0 | | | | | 5.0 g Product | | | | | | | | |
| IX | | C₃⁻55.0 | 9.78 | 66.13 | — | 0.18 | 1.57 | 7.88 | 9.34 | 1.04 | 3.50 | 0.59 | — | 33.7 | 61.3 |
| X | 1st | C₃⁻72.8 | — | — | — | 12.58 | 44.40 | — | 13.89 | 2.50 | — | — | 26.63 | 54.7 | 75.2 |
| | 2nd | C₃⁻52.0 | — | — | — | 14.23 | 51.74 | — | 15.88 | 1.47 | — | — | 16.70 | 38.9 | 74.8 |

TABLE IB-continued

| Example No. | Run No. | Feed g | iC$_4$ | nC$_4$ | C$_5$s | 2.3DMC$_4$ | 2MC$_5$ | 3MC$_5$ | nC$_6$ | Unidentified | 3MC$_7$ | nC$_8$ | C$_9$ | Total Product wt. g. | Conversion % |
|---|---|---|---|---|---|---|---|---|---|---|---|---|---|---|---|
| | 3rd | C$_2$=87.0 | — | 60.75 | 2.09 | 2.17 | 7.55 | 9.30 | 8.60 | — | 9.56 | — | — | 63.7 | 73.3 |
| | 4th | iC$_4$=84.0 | | | | | | 5.0 g Product | | | | | | | |
| XI | | C$_3$=72.8 | — | — | — | 13.87 | 51.75 | — | 16.80 | 6.38 | — | — | 11.20 | 39.7 | 54.4 |
| XII | | C$_3$=70.2 | | | | | | 26.0 g Product | | | | | | | |
| XIII | | C$_3$= | | | | | | No Reaction | | | | | | | |

EXAMPLE XIV

Both 1.83 millimoles of bis(triphenylphosphine) nickel dicarbonyl and 4.0 g. extrudate pellets of Example III were weighed into a 300 cc autoclave along with 50 ml. toluene. These components were stirred vigorously under a nitrogen atmosphere at 80°–120° F. for 15 minutes. Immediately after, 100 ml. butadiene was added to the system. The reactor was pressured at a constant ethylene pressure, 750 psig. Reaction was continued at 160° F. for a 4-hour period. The product was analyzed by means of a gas chromatographic technique. Tables III and IV list details of the results obtained in this run. About 47% of the product was composed of various hexadiene products such as 1,4-trans-; 1,4-cis; 2-trans, 4-trans-; 2-cis- 4-trans-hexadiene. Besides hexadiene products, 3-methylheptadiene (a codimer of conjugated 2,4-hexadiene product and an additional ethylene molecule) and 4-vinyl-1-cyclohexene (a homodimer of butadiene) were also obtained along with a large portion of heavier molecular weight product (37%). Analysis of the heavy product was not attempted. 2,4-Hexadienes are products resulting from the isomerization of the initial 1,4-hexadiene products. These 2,4-hexadienes, conjugated dienes, tend to react with an additional ethylene molecule to produce 3-methylheptadiene.

EXAMPLE XV

The same reaction cited in Example XIV was repeated under slightly different conditions. Reaction of 1,3-butadiene (120 ml.) with ethylene was allowed to proceed at 800 psig ethylene pressure at 116°–120° F. for an hour. The product distribution obtained from this run is quite similar to that obtained from the initial run. Results from this run are also listed in Tables II and III.

EXAMPLE XVI 1,3-Butadiene (100 ml.) was fed to a system consisting of 0.87 millimoles of bis(triphenylphosphine) nickel dicarbonyl and 10.0 g extrudate of Example III in 30 ml. toluene in a 300 cc stainless steel bomb. Ethylene was fed to the reactor under 800 psig and was rapidly absorbed when the bomb was submerged in an oil bath set at 150° F. A clear colorless reaction mixture was removed from the reactor after the reaction has proceeded for 30 minutes. Products were analyzed by gas chromatography, as listed in Tables III and IV. The product was composed of about 33% of hexadiene isomer products, 14% 4-vinyl-1-cyclohexene, 46% of heavy product and a small amount of 3-methylheptadiene (1.2%). The solid catalyst left inside of the bomb was saved for two more consecutive runs.

In the second run, 100 ml. of 1,3-butadiene was added to the solid catalyst aged from the first run, followed immediately by addition of ethylene. The system was maintained under an 800 psig ethylene pressure at 150° F. for 2 hours. The product distribution obtained in this run was quite similar to that obtained in the first run. Due to the tendency of the catalyst pellets to absorb some of the surrounding liquid, it was impossible to discharge the reaction liquid quantitatively from the reactor. Thus, carry-over from the preceding run(s) was unavoidable throughout these consecutive runs made with the solid catalyst pellets.

The third run was made with 115 ml. 1,3-butadiene under 800–240 psig ethylene pressure at 144° F. for a 1** hour period. Details of the run are listed in Tables III and IV. It seems clear from the results obtained in these three consecutive runs that the catalytic species was firmly held on the support and that catalytic activity was still maintained at an equal level even after these consecutive runs over a 5¼ hour period.

Three separate runs were made an order to study the reaction of butadiene with the present catalyst systems. They are described in Examples XVII to XIX.

EXAMPLE XVII

In Run A, 1.25 millimoles of bis(triphenylphosphine) nickel dicarbonyl was dissolved in 40 ml. toluene and introduced into a 300 cc stainless steel bomb. The butadiene substrate (100 ml.) was fed to the solution, and the reactor was kept in an oil bath set at 162°–182° F for 3½ hours. During this period, the pressure of the reaction increased from 180 psig to 340 psig. No significant reaction was noticed in this system without support material. It was shown by mass spectroscopic analysis that a very limited amount of butadiene homodimer was present in the discharged reaction mixture. It was also learned from related work that bis(triphenylphosphine) nickel dicarbonyl solution in an inert solvent was inactive for the cross-dimerization of 1,3-butadiene and ethylene in the absence of the support material.

EXAMPLE XVIII

Run B employed the catalyst system containing 0.85 millimole of bis(triphenylphosphine) nickel dicarbonyl and 10.0 g extrudate of Example III in 30 ml. toluene in a 300 cc bomb. The catalyst system was vigorously agitated at room temperature for 20 minutes, and then the whole bomb was submerged in an oil bath set at 158° F. for about 10 minutes. 1,3-Butadiene (110 ml.) was fed to the system, and allowed to react for about an hour. A viscous liquid polymer of polybutadiene having low molecular weight was obtained. The support material was thus an essential catalytic component in creation of an active catalytic species from bis(triphenylphosphine) nickel dicarbonyl for the polymerization of 1,3-butadiene.

EXAMPLE XIX

In Run C a white rubbery polymer was obtained from 1,3-butadiene with the catalyst system consisting of 1.13 millimoles of bis(triphenylphosphine) nickel dicarbonyl, and 4.5 g. pellets of Example III in 40 ml. toluene. Reaction conditions were quite similar to those used in Run B except the span of reaction time was extended from 1 hour to 4 hours. In short, bis(triphenylphosphine) nickel dicarbonyl alone exhibited no significant catalytic activity for the butadiene reaction, while bis(triphenylphosphine) nickel dicarbonyl with support material showed a substantial catalytic effect for the polymerization of butadiene.

TABLE II

| Example No. | Run No. | Catalyst Composition $(\phi P)_2Ni(CO)_2$ m moles | Support g. | Solvent ml toluene | Catalyst Aged hr. | Reaction Conditions Pressure psig | Temperature °F. | Time hr. |
|---|---|---|---|---|---|---|---|---|
| XIV | — | 1.83 | 4.0 | 50 | — | 750 | 160 | 4 |
| XV | — | 0.85 | 4.5 | 30 | — | 800 | 116–120 | 1 |
| XVI | 1st | <0.87 | 10.0 | 30 | — | 800 | 150 | ½ |
|  | 2nd | <0.87 | 10.0 | — | ½ | 780 | 150 | 2 |
|  | 3rd | <0.87 | 10.0 | — | 3 | 800–240 | 144 | 1¼ |
| XVII | | 1.25 | — | 40 | — | 340–180 | 162–182 | 3½ |
| XVIII | | 0.85 | 10.0 | 30 | — | 205–135 | 158 | 1 |
| XIX | | 1.13 | 4.5 | 40 | — | 73–172 | 138–196 | 4 |

Table III

| Example No. | 2 No. | Feed g. | 1,5 | 1,4t | $C_6^{--}$ 1,4c | 2t,4t | 2c,4t | 2c,4c | Total g. | $C_6^{--}$ wt. % | Unknown | 3MC$_7^{--}$ | 4VCyC$_6^{--}$ | Heavy Prod. | Total Prod. g. |
|---|---|---|---|---|---|---|---|---|---|---|---|---|---|---|---|
| | | | wt. % | | | | | | | | wt. % | | | | |
| XIV | — | $C_2^{--}$ +BD 62.7 | 2.1 | 30.6 | 12.5 | 2.6 | 2.4 | 0.4 | 8.3 | 46.9 | 5.1 | 1.5 | 5.6 | 37.2 | 17.8 |
| XV | — | $C_2^{--}$ +BD 75.2 | 0.9 | 26.8 | 16.8 | 3.5 | 3.7 | 0.6 | 6.0 | 52.2 | — | 2.4 | 14.8 | 30.5 | 11.5 |
| XVI | 1st | $C_2^{--}$ +BD 62.7 | 0.1 | 15.6 | 12.0 | 1.7 | 2.4 | 0 | 2.5 | 33.0 | 7.5 | 1.2 | 4.0 | 45.6 | 7.6 |
| | 2nd | $C_2^{--}$ +BD 62.7 | 0.8 | 15.3 | 10.8 | 2.0 | 2.4 | 0.4 | 3.3 | 31.5 | 4.0 | 1.6 | 20.3 | 42.5 | 10.5 |
| | 3rd | $C_2^{--}$ +BD 72.1 | — | 18.9 | 13.1 | 1.4 | 1.7 | 0.3 | 3.8 | 35.4 | — | 0.8 | 18.9 | 44.8 | 10.8 |
| XVII | | BD 62.7 no significant reaction. | | | | | | | | | | | | | |
| XVIII | | BD 72.1 small portion of poly BD obtained. | | | | | | | | | | | | | |
| XIX | | BD 62.7 white poly BD polymer. | | | | | | | | | | | | | |

It is claimed:

1. In a process for the codimerization of alphaolefins of 2 to 10 carbon atoms and 1,3-conjugated dienes of 4 to about 12 carbon atoms, the improvement which comprises conducting the polymerization in contact with a catalytically effective amount of a catalyst composition comprising:

a. a minor, catalytically effective amount of a nickel complex of the formula $(L)_m Ni(CO)_n$ wherein L is a tertiary, hydrocarbyl-substituted monodentate ligand of a Group V-A element, $m$ is an integer having a value from 1 to 3 and $n$ is an integer having a value of 1 to 4 the sum of $m$ and $n$ being 4; and b. a major amount of an acidic, solid, silica-based support material as an essential catalyst component.

2. A process of claim 1 wherein the weight ratio of (b) to (a) is from about 2 to 2000:1.

3. A process of claim 1 wherein the nickel complex is a bis(tertiary, hydrocarbyl-substituted monophosphine) nickel dicarbonyl complex.

4. A process of claim 3 wherein each hydrocarbyl substituent of the monophosphine is a hydrocarbyl group of up to about 20 carbon atoms.

5. A process of claim 4 wherein each hydrocarbyl group is phenyl.

6. A process of claim 5 wherein the weight ratio of (b) to (a) is from about 5 to 200:1.

7. A process of claim 1 wherein the silica-based support material is calcined and has a separate, additional alumina phase.

8. A process of claim 6 wherein the silica-based support material is calcined, has a separate, additional alumina phase and has a surface area of about 150 to 400 square meters per gram.

9. A process of claim 1 wherein the support is comprised of about 45 to 95 weight percent amorphous silica-alumina and about 5 to 55 weight percent of a separate alumina phase, the total alumina content of said support being about 20 to 70 weight percent.

10. A process of claim 9 wherein said alumina results from the calcination of a member selected from the group consisting of amorphous hydrous alumina, alumina monohydrate and mixtures thereof.

11. A process of claim 1 wherein the support is comprised of about 45 to 95 weight percent amorphous silica-alumina and about 5 to 55 weight percent of a separate alumina phase, the total alumina content of said support being about 20 to 70 weight percent, the 1,3-conjugated diene is 1,3-butadiene and the alpha olefin has the structural formula RCH=CH$_2$, wherein R is lower alkyl.

12. A process of claim 11 wherein said alumina results from the calcination of a member selected from the group consisting of amorphous hydrous alumina, alumina monohydrate and mixtures thereof.

13. A process of claim 3 wherein the support is comprised of about 45 to 95 weight percent amorphous silica-alumina and about 5 to 95 weight percent of a separate alumina phase, the total alumina content of said support being about 20 to 70 weight percent.

14. A process of claim 13 wherein said alumina results from the calcination of a member selected from the group consisting of amorphous hydrous alumina, alumina monohydrate and mixtures thereof.

15. A process of claim 5 wherein the support is comprised of about 45 to 95 weight percent amorphous silica-alumina and about 5 to 55 weight percent of a separate alumina phase, the total alumina content of said support being about 20 to 70 weight percent.

16. A process of claim 5 wherein said alumina results from the calcination of a member selected from the group consisting of amorphous hydrous alumina, alumina monohydrate and mixtures thereof.

17. A process of claim 6 wherein the support is comprised of about 45 to 95 weight percent amorphous silica-alumina and about 5 to 55 weight percent of a separate alumina phase, the total alumina content of said support being about 20 to 70 weight percent.

18. A process of claim 17 wherein said alumina results from the calcination of a member selected from the group consisting of amorphous hydrous alumina, alumina monohydrate and mixtures thereof.

* * * * *